(12) United States Patent
Ogata et al.

(10) Patent No.: US 9,561,073 B2
(45) Date of Patent: *Feb. 7, 2017

(54) ENERGY FACILITATED COMPOSITION DELIVERY

(75) Inventors: Wayne Ogata, San Ramon, CA (US); Osamu Katoh, Toyohashi (JP)

(73) Assignee: RetroVascular, Inc., Pleasanton, CA (US)

( * ) Notice: Subject to any disclaimer, the term of this patent is extended or adjusted under 35 U.S.C. 154(b) by 624 days.

This patent is subject to a terminal disclaimer.

(21) Appl. No.: 13/560,841

(22) Filed: Jul. 27, 2012

(65) Prior Publication Data
US 2012/0296262 A1 Nov. 22, 2012

Related U.S. Application Data

(63) Continuation-in-part of application No. PCT/US2011/031018, filed on Apr. 1, 2011, and a
(Continued)

(51) Int. Cl.
*A61B 18/18* (2006.01)
*A61B 18/14* (2006.01)
(Continued)

(52) U.S. Cl.
CPC ........ *A61B 18/1492* (2013.01); *A61B 18/1815* (2013.01); *A61B 18/24* (2013.01);
(Continued)

(58) Field of Classification Search
CPC ............ A61B 18/18; A61B 2018/1815; A61B 2018/1861
(Continued)

(56) References Cited

U.S. PATENT DOCUMENTS

| 3,868,956 A | 3/1975 | Alfidi et al. |
| 5,041,109 A | 8/1991 | Abela |

(Continued)

FOREIGN PATENT DOCUMENTS

| JP | 2004/500171 | 1/2004 |
| JP | 2006/263125 | 10/2006 |

(Continued)

OTHER PUBLICATIONS

Apr. 8, 2010 Office Examination Report issued by the Australian Patent Office on Application No. 2007215224, pp. 1-2.
(Continued)

*Primary Examiner* — Aaron Roane
(74) *Attorney, Agent, or Firm* — LeClairRyan, a Professional Corporation

(57) ABSTRACT

A device for delivering a composition to a hollow body region is disclosed. In one aspect, the device comprises a first longitudinal member and a second longitudinal member. Both of the longitudinal members may comprise conductive electrodes. The longitudinal members are further configured to be connected to an energy source such that the conductive electrodes are configured to generate an energy field. At least one of the longitudinal members further comprises a delivery element configured to deliver at least one composition to the body region, such that the composition is delivered in a direction that is influenced by the generated energy field. In one aspect, the body region is a vessel comprising an occlusion.

18 Claims, 12 Drawing Sheets

Related U.S. Application Data continuation-in-part of application No. 12/753,844, filed on Apr. 2, 2010, now Pat. No. 9,283,034, which is a continuation-in-part of application No. 12/680,500, filed as application No. PCT/US2008/077403 on Sep. 23, 2008, now Pat. No. 8,911,435.

(60) Provisional application No. 60/975,473, filed on Sep. 26, 2007, provisional application No. 61/298,547, filed on Jan. 26, 2010.

(51) Int. Cl.
  A61B 18/24 (2006.01)
  A61B 18/00 (2006.01)
  A61N 7/02 (2006.01)
  A61B 17/3207 (2006.01)

(52) U.S. Cl.
  CPC ............ *A61B 2017/320716* (2013.01); *A61B 2018/0041* (2013.01); *A61B 2018/1472* (2013.01); *A61B 2018/1861* (2013.01); *A61B 2090/378* (2016.02); *A61N 7/022* (2013.01)

(58) Field of Classification Search
  USPC ................................................ 606/41–49
  See application file for complete search history.

(56) References Cited

U.S. PATENT DOCUMENTS

| | | | |
|---|---|---|---|
| 5,188,635 | A | 2/1993 | Radtke |
| 5,366,443 | A | 11/1994 | Eggers et al. |
| 5,419,767 | A | 5/1995 | Eggers et al. |
| 5,429,131 | A | 7/1995 | Scheinman |
| 5,501,694 | A | 3/1996 | Ressemann et al. |
| 5,514,128 | A | 5/1996 | Hillsman et al. |
| 5,624,430 | A | 4/1997 | Eton et al. |
| 5,695,517 | A | 12/1997 | Marin et al. |
| 5,851,185 | A | 12/1998 | Berns |
| 5,895,398 | A | 4/1999 | Wensel et al. |
| 6,068,645 | A | 5/2000 | Tu |
| 6,235,044 | B1 | 5/2001 | Root et al. |
| 6,416,523 | B1 | 7/2002 | Lafontaine et al. |
| 6,454,775 | B1 | 9/2002 | Demarais et al. |
| 6,697,863 | B1 | 2/2004 | Egawa |
| 6,911,026 | B1 | 6/2005 | Hall et al. |
| 6,936,056 | B2 | 8/2005 | Nash et al. |
| 7,037,316 | B2 | 5/2006 | McGuckin et al. |
| 7,297,145 | B2 * | 11/2007 | Woloszko et al. ............ 606/41 |
| 7,918,859 | B2 | 4/2011 | Katoh et al. |
| 8,545,418 | B2 | 10/2013 | Heuser |
| 8,911,435 | B2 * | 12/2014 | Katoh et al. .................... 606/34 |
| 2002/0052602 | A1 | 5/2002 | Wang |
| 2002/0058939 | A1 | 5/2002 | Wagner et al. |
| 2003/0028200 | A1 | 2/2003 | Berg et al. |
| 2003/0065316 | A1 | 4/2003 | Levine et al. |
| 2004/0082962 | A1 | 4/2004 | Demarais et al. |
| 2004/0230219 | A1 | 11/2004 | Roucher, Jr. et al. |
| 2005/0154400 | A1 | 7/2005 | Katoh et al. |
| 2005/0171478 | A1 | 8/2005 | Selmon et al. |
| 2005/0251134 | A1 | 11/2005 | Woloszko et al. |
| 2006/0079880 | A1 | 4/2006 | Sage et al. |
| 2006/0224112 | A1 | 10/2006 | Lentz |
| 2007/0043389 | A1 | 2/2007 | Shindelman |
| 2007/0049867 | A1 | 3/2007 | Shindelman |
| 2007/0112342 | A1 | 5/2007 | Pearson et al. |
| 2007/0173878 | A1 | 7/2007 | Heuser |
| 2007/0208368 | A1 | 9/2007 | Katoh et al. |
| 2007/0293846 | A1 | 12/2007 | Von Oepen et al. |
| 2008/0039830 | A1 | 2/2008 | Munger et al. |
| 2008/0039935 | A1 | 2/2008 | Buch et al. |
| 2008/0154153 | A1 | 6/2008 | Heuser |
| 2008/0306499 | A1 | 12/2008 | Katoh et al. |
| 2008/0312673 | A1 | 12/2008 | Viswanathan et al. |
| 2009/0192508 | A1 | 7/2009 | Laufer et al. |
| 2010/0256616 | A1 | 10/2010 | Katoh et al. |
| 2013/0072957 | A1 | 3/2013 | Anderson |

FOREIGN PATENT DOCUMENTS

| | | |
|---|---|---|
| JP | 2007/195599 | 8/2007 |
| WO | WO 9713471 | 4/1997 |
| WO | WO 00/09020 | 2/2000 |
| WO | WO 01/39673 | 6/2001 |
| WO | WO 2009/042614 | 4/2009 |

OTHER PUBLICATIONS

Apr. 8, 2011 Filed Response to Apr. 8, 2010 Examination Report issued on Australian Patent Application No. 2007215224, pp. 1-15.
Apr. 29, 2011 Notice of Allowance issued by Australian Patent Office on Australian Patent Application No. 2007215224, pl. 1.
Feb. 22, 2011 Examination Report issued on Australian Patent Application No. 2008304599 issued by the Australian Patent Office, pp. 1-4.
Jul. 20, 2012 Filed Response to Feb. 22, 2011 Examination Report issued on Australian Patent Application No. 2008304599, pp. 1-20.
Sep. 4, 2012 Examination Report issued on Australian Patent Application No. 2008304599 issued by the Australian Patent Office, pp. 1-4.
Oct. 11, 2012 Filed Response to Sep. 4, 2012 Second Examination Report issued on Australian Patent Application Serial No. 208304599, pp. 1-7.
Mar. 1, 2012 Examination Report issued on Australian Patent Application No. 2009239406 issued by the Australian Patent Office, pp. 1-2 Abandoned.
May 25, 2012 Office Action issued by Canadian Patent Office on Canadian Patent Application No. 2,722,486, pp. 1-3.
Nov. 23, 2012 Filed response to May 25, 2012 Office Action issued by Canadian Patent Office on Canadian Patent Application No. 2,722,486, pp. 1-4.
May 14, 2010 Office Action issued by Canadian Patent Office on Canadian Patent Application No. 2,641,729, pp. 1-3.
Nov. 15, 2010 Filed Response to May 14, 2012 Official Action issued by Canadian Patent Office on Canadian Patent Application No. 2,641,729, pp. 1-13.
Feb. 28, 2011 Office Action issued by Canadian Patent Office on Canadian Patent Application No. 2,641,729, pp. 1-3.
Aug. 22, 2011 Filed Response to Feb. 28, 2011 Official Action issued by Canadian Patent Office on Canadian Patent Application No. 2,641,729, pp. 1-24.
Jan. 12, 2012 Office Action issued by Canadian Patent Office on Canadian Patent Application No. 2,641,729, pp. 1-3.
Jul. 11, 2012 Filed Response to Jan. 12, 2012 Official Action issued by Canadian Patent Office on Canadian Patent Application No. 2,641,729, pp. 1-9.
Jul. 24, 2012 Extended Supplementary European Search Report, issued by the European Patent Office for European Patent Application Serial No. 08834456.9, pp. 1-9.
Nov. 19, 2012 Filed Response to Jul. 24, 2012 Extended Supplementary European Search Report, issued by the European Patent Office for European Patent Application Serial No. 08834456.9, pp. 1-10.
Feb. 24, 2011 Supplementary European Search Report, issued by the European Patent Office for European Patent Application Serial No. 09734649.8, pp. 1-6.
Sep. 26, 2011 Filed Response to Feb. 24, 2011 Search Opinion issued by the European Patent Office for European Patent Application Serial No. 09734649.8, pp. 1-8.
Nov. 23, 2011 Examination Report issued by the European Patent Office for European Patent Application Serial No. 09734649.8, pp. 1-3.
Feb. 7, 2012 European Associate's Comments in Reply to Communication Pursuant to Article 94(3) issued by the European Patent Office for European Patent Application Serial No. 09734649.8, pp. 1-2.

(56) References Cited

OTHER PUBLICATIONS

Jun. 4, 2012 Filed Response to Nov. 23, 2011 Examination Report issued by the European Patent Office for European Patent Application Serial No. 09734649.8, pp. 1-4.
Dec. 10, 2012 Decision to Refuse European Application issued by the European Patent Office for European Patent Application Serial No. 09734649.8, pp. 1-8.
Nov. 23, 2010 Non-Final Rejection issued by Korean Patent Office on Korean Application No. 10-2008-7022167, pp. 1-6.
Jan. 24, 2011 Filed Response to Nov. 23, 2010 Non-Final Rejection issued by Korean Patent Office on Korean Application No. 10-2008-7022167, pp. 1-26.
Jul. 20, 2011 Notice of Allowance issued by Korean Patent Office on Korean Application No. 10-2008-7022167, pp. 1-3.
May 18, 2012 Instructions for Response to Dec. 19, 2011 Non-Final Rejection issued by Korean Patent Office on Korean Application No. 10-2010-7008803, pp. 1-5.
Oct. 29, 2012 Notice of Allowance issued by Korean Patent Office on Korean Application No. 10-2010-7008803, pp. 1-3.
May 31, 2011 Office Action issued by Japanese Patent Office on Japanese Patent Application No. 2008-554416, pp. 1-4.
Jul. 26, 2011 Filed Response to May 31, 2011 Office Action issued by Japanese Patent Office on Japanese Patent Application No. 2008-554416, pp. 1-3.
Mar. 28, 2012 Certificate of Patent issued Feb. 24, 2012 by Japanese Patent Office on Japanese Patent Application No. 2008-554416, pp. 1-3.
Jun. 15, 2012 Notice of Reason for Rejection issued by Japanese Patent Office on Japanese Patent Application No. 2011-506400, pp. 1-8.
Sep. 17, 2012 Instructions for Response to Jun. 15, 2012 Notice of Reason for Rejection (Decision of Rejection) issued by Japanese Patent Office on Japanese Patent Application No. 2011-506400, pp. 12.
Nov. 6, 2012 Decision of Rejection issued by Japanese Patent Office on Japanese Patent Application No. 2011-506400, pp. 1-5.
Dec. 27, 2012 Foreign Associates Comments on Nov. 6, 2012 Decision of Rejection issued by Japanese Patent Office on Japanese Patent Application No. 2011-506400, pp. 1-6.
Sep. 22, 2008 International Search Report for PCT Application No. PCT/US2007/03706, pp. 1-2.
Oct. 21, 2008 International Preliminary Report on Patentability with Written Opinion issued on PCT Application No. PCT/US2007/003706, pp. 1-4.
Dec. 1, 2008 International Search Report issued for PCT Application No. PCT/US2008/077403, p. 1.
Jul. 7, 2009 International Search Report issued for PCT Application No. PCT/US2009/041287, pp. 1-2.
Jun. 14, 2011 International Search Report and Written Opinion issued on PCT Application No. PCT/US2011/031018, pp. 1-7.
May 12, 2010 Office Action for U.S. Appl. No. 11/706,041, pp. 1-11.
Nov. 26, 2010 Notice of Allowance in U.S. Appl. No. 11/706,041, pp. 1-6.
Nov. 18, 2010 Office Action for U.S. Appl. No. 12/150,111, pp. 1-10.
Feb. 18, 2011 Filed Response to Nov. 18, 2010 Office Action for U.S. Appl. No. 12/150,111, pp. 1-10.
Apr. 22, 2011 Final Office Action for U.S. Appl. No. 12/150,111, pp. 1-8.
Jul. 22, 2011 Filed Response to Apr. 22, 2011 Final Office Action for U.S. Appl. No. 12/150,111, pp. 1-9 with RCE.
Feb. 13, 2013 Office Action for U.S. Appl. No. 12/753,844, pp. 1-15.
Feb. 4, 2013 Office Action for U.S. Appl. No. 13/037,304, pp. 1-15.
Aug. 8, 2013 Extended European Search for European Patent Application No. 11763547.4.
Bolia, A. et al., "Recanalization of Iliac Artery Occlusion by Subintimal Dissection Using the Ipsilateral and the Contralateral Approach", Clinical Radiology, vol. 52, 1997, 684-687.
Bourassa, Martial G. et al., "Bypass Angioplasty Revascularization Investigation: Patient Screening, Selection, and Recruitment", The American Journal of Cardiology, vol. 75, Issue 9, 1995, 3C-8C.
Columbo, Antonio et al., "Treating Chronic Total Occlusions Using Subintimal Tracking and Reentry: The STAR Technique", Catheterization and Cardiovascular Interventions, vol. 64, No. 4, 2005, 407-411.
Ito, Shigenori et al., "Novel Technique Using Intravascular Ultrasound-Guided Guidewire Cross in Coronary Intervention for Uncrossable Chronic Total Occlusions", Circulation Journal, vol. 68, No. 11, Nov. 2004, 1088-1092.
Kimura, Bruce J. et al., "Subintimal Wire Position During Angioplasty of a Chronic Total Coronary Occlusion: Detection and Subsequent Procedural Guidance by Intravascular Ultrasound", Catheterization and Cardiovascular Diagnosis, vol. 35, No. 3, 1997, 262-265.
King, Spencer B. et al., "A Randomized Trial Comparing Coronary Angioplasty With Coronary Bypass Surgery. Enjoy Angioplasty Versus Surgery Trial (EAST)", The New England Journal of Medicine; vol. 331, Oct. 20, 1994, 1044-1050.
Kinoshita, Isao et al., "Coronary Angioplasty of Chronic Total Occlusions With Bridging Collateral Vessels: Immediate and Follow-Up Outcome From a Large Single-Center Experience", Journal of the American College of Cardiology, vol. 26, No. 2, Aug. 1995, 409-415.
Matsubara, Tetsuo et al., "IVUS-Guided Wiring Technique: Promising Approach for the Chronic Total Occlusion", Catheterization and Cardiovascular Interventions, vol. 61, No. 3, 2004, 381-386.
Melchior, Jean-Paul et al., "Improvement of Left Ventricular Contraction and Relaxation Synchronism After Recanalization of Chronic Total Coronary Occlusion by Angioplasty", Journal of the American College of Cardiology, vol. 9, No. 4, Apr. 1987, 763-768.
Olivari, Zoran et al., "Immediate Results and One-Year Clinical Outcome After Percutaneous Coronary Interventions in Chronic Total Occlusions: Data From a Multicenter, Prospective. Observational Study (TOAST-GISE)", Journal of the American College of Cardiology, vol. 41, No. 10, 2003, 1672-1678.
Spinosa, David J. et al., "Simultaneous Antegrade and Retrograde Access for Subintimal Recanalization of Peripheral Arterial Occlusion", J. Vasc. Interv. Radiol.; vol. 14, 2003, 1449-1454.
Suero, James A. et al., "Procedural Outcomes and Long-Term Survival Among Patients Undergoing Percutaneous Coronary Intervention of a Chronic Total Occlusion in Native Coronary Arteries: A 20 year Experience", Journal of the American College of Cardiology, vol. 38, No. 2, 2001, 409-414.

\* cited by examiner

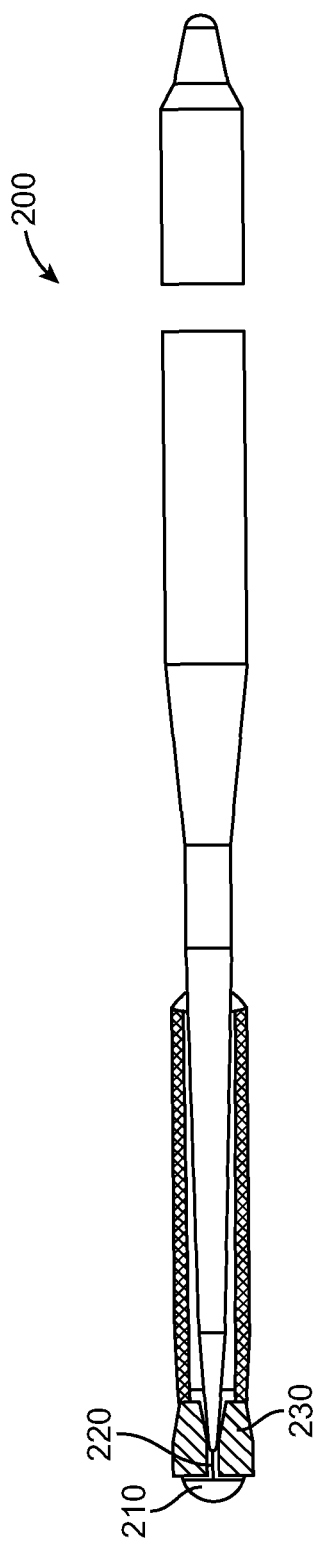
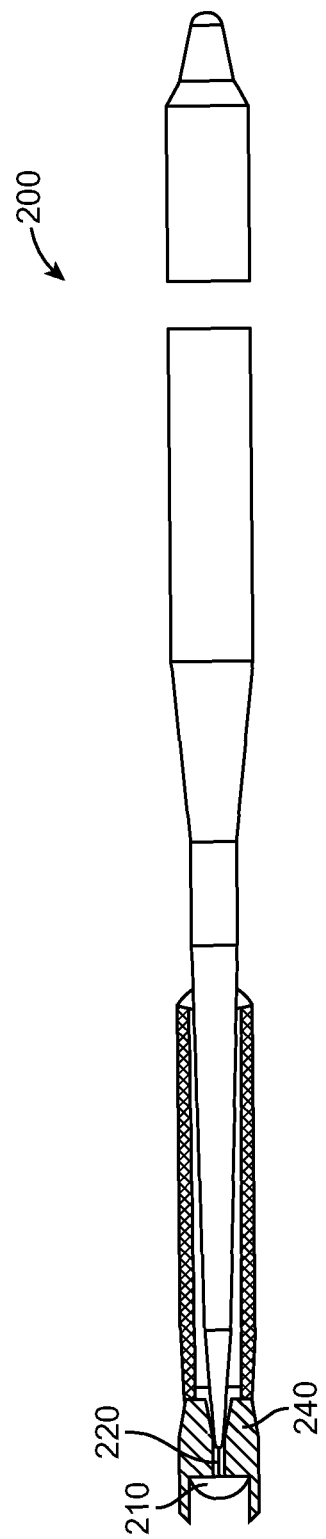
FIG. 3A
FIG. 3B

ENERGY FACILITATED COMPOSITION DELIVERY

CROSS-REFERENCES TO RELATED APPLICATIONS

This application is a continuation-in-part application of PCT/US2011/031018 filed Apr. 1, 2011, titled "Recanalizing Occluded Vessels Using Radiofrequency Energy", which claims priority from U.S. application Ser. No. 12/753,844, filed Apr. 2, 2010, titled "Recanalizing Occluded Vessels Using Radiofrequency Energy". This application is also a continuation-in-part application of U.S. application Ser. No. 12/753,844, filed Apr. 2, 2010, titled "Recanalizing Occluded Vessels Using Radiofrequency Energy", which is a continuation-in-part of U.S. application Ser. No. 12/680,500, a national stage application under 35 U.S.C. §371, filed Mar. 26, 2010, titled "Recanalizing Occluded Vessels Using Radiofrequency Energy", which claims priority from PCT Application No. PCT/US2008/077403, filed Sep. 23, 2008, which claims the priority benefit of U.S. Provisional Application No. 60/975,473, filed Sep. 27, 2007. U.S. application Ser. No. 12/753,844 also claims priority to U.S. Provisional Application Ser. No. 61/298,547, filed on Jan. 26, 2010, titled "Recanalizing Occluded Vessels Using Radiofrequency Energy". The disclosures of the above related applications are incorporated herein by reference.

FIELD OF THE INVENTION

Present embodiments relate generally to delivering a composition to a treatment region in the body under the influence of an energy field. Specifically, present embodiments relate to delivering a composition to an occluded vessel to aid or facilitate the crossing of severe or total chronic occlusions of lumens in the body.

DESCRIPTION OF THE RELATED ART

Chronic total occlusion (CTO) is the complete blockage of a vessel and may have serious consequences if not treated in a timely fashion. The blockage could be due to atheromatous plaque or old thrombus. One of the common procedures for treating CTOs of the coronary arteries is percutaneous transluminal coronary angioplasty (PTCA). During a PTCA procedure, a small incision is typically made in the groin. A guiding catheter over a guidewire is introduced into the femoral artery and advanced to the occlusion. At times, with gentle maneuvering, the guidewire is able to cross the occlusion. A balloon-tipped angioplasty catheter is then advanced over the guidewire to the occlusion. The balloon is inflated, separating or fracturing the atheroma. Often times, a stent is subsequently or simultaneously deployed. Some of the common steps involved in the PTCA procedure for CTOs are the simultaneous injection of a contrast agent in the contra-lateral vessel, securing backup force or stabilization for a guidewire (which could invoke additional personnel to handle the catheter), puncturing the plaque, drilling or rotating the guidewire to push it through the dense plaque, etc. Because of the stiff resistance sometimes offered by dense plaque, one could be forced to use stiff wires. Occasionally, the wires could puncture the vessel wall calling for remedial measures.

The most common percutaneous coronary intervention (PCI) failure mode for CTOs is inability to successfully pass a guidewire across the lesion into the true lumen of the distal vessel. To date, there is no consensus on how best to treat CTO after attempts with conventional guidewires have failed. Different strategies for CTOs have been developed including the side branch technique, the parallel wire technique, and the IVUS guided technique. Mechanical and energy based devices have also been proposed for passing guidewires through hard calcified occlusions, such as mechanical cutting or oscillation and laser or ultrasound or radiofrequency (RF) energy ablation. Each of these devices works by strictly utilizing an antegrade approach and locally applying energy (typically in the form of heat) at the tip of the guidewire or catheter device in order to create a channel and hopefully enter the distal true lumen.

RF energy is widely used to coagulate, cut or ablate tissue. In both modalities, monopolar and bipolar, conductive electrodes contact the tissue to be treated. In the monopolar mode, the active electrode is placed in contact with the tissue to be treated and a return electrode with a large surface area is located on the patient at a distance from the active electrode. In the bipolar mode, the active and return electrodes are in close proximity to each other bracketing the tissue to be treated. Sometimes an array of electrodes is used to provide better control over the depth of penetration of the RF field and hence control over the temperatures to which the tissue is heated. There are many disadvantages with each mode. For example, in the monopolar arrangement, because of the large physical separation between the electrodes there are frequent reports of local burning at the electrode sites. This would clearly be undesirable where one of the electrodes will be inside a blood vessel. The other serious issue is the likelihood of forming blood clots. The tissue that is in contact with the electrodes can be coagulated or ablated. In the case of the electrodes being present inside a blood vessel, the formation of dangerous blood clots would obviously be undesirable.

In an attempt to overcome the issues described above, various device and electrode configurations are described in the following patents. U.S. Pat. Nos. 5,366,443 and 5,419,767 describe the use of RF electrodes on a catheter to cross a lesion. These patents describe a bipolar electrode assembly at the distal tip of a catheter that is in contact with the occlusion, and patentees state that application of RF energy ablates the occlusion and renders the occlusion susceptible for the guidewire to penetrate. This method has the drawback that careful tracking of the occlusion and the ablation process is necessary to avoid trauma to the vessel walls or healthy tissue, since the possibility of short-circuiting of current through healthy tissue instead of the occlusion is high. U.S. Pat. No. 5,419,767 overcomes this limitation to a certain extent through the use of a multiple electrode array. However, this device requires a channel to be pre-created through the occlusion so that the device can be passed through a guidewire traversing this channel, which is not always easy.

U.S. Pat. No. 5,514,128 to Hillsman et al. describes a laser catheter device that enables ablation of an occlusion in the vasculature. This system has similar drawbacks to the ones described above—need for a guidance system, potential for healthy tissue to be ablated, complexity (and hence cost) of the device, etc.

One major problem with the existing devices is the potential for the ablation energy to damage the walls of the vasculature, in the absence of a mechanism to track the orientation and position of the energy delivery member. Several devices exist in the prior art that address the issue of tracking and steering of the energy delivery element. U.S. Pat. No. 6,911,026 to Hall et al. describes a magnetic steering and guidance system to direct an ablation device that delivers RF energy at the tip in a unipolar configuration where the return electrode is placed externally in contact with the body or in a bipolar configuration where the return electrode is a ring surrounding the central wire electrode.

U.S. Pat. No. 6,416,523 to Lafontaine discusses a mechanical cutting device where the guidance is provided by measuring impedance of the tissue in contact. The guidance system senses the difference in impedance between the stenotic tissue and the vessel wall and directs the cutting element to the occlusion.

However, none of these alternate strategies have provided satisfactory results for the most challenging of the CTOs. In case of hard calcified occlusions, the revascularization procedure can be tedious and time consuming. Therefore, there is a need for improved methods of ablating or disrupting the occlusive material that are safe, efficacious and fast. It would be beneficial to have alternate techniques and devices that would recanalize a CTO without the shortcomings of the current techniques.

SUMMARY OF THE INVENTION

Various methods, devices, and systems configured to deliver a composition to a treatment region are disclosed. In one aspect, present embodiments are configured to deliver one or more compositions to an occluded vessel to aid in the treatment and recanalization of an occlusion.

In one aspect, a device for delivering a composition to a hollow body region comprising a first longitudinal member and a second longitudinal member. Both of the longitudinal members may comprise conductive electrodes. The longitudinal members are further configured to be connected to an energy source such that the conductive electrodes are configured to generate an energy field. At least one of the longitudinal members further comprises a delivery element configured to deliver at least one composition to the body region, such that the composition is delivered in a direction that is influenced by the generated energy field. In one aspect, the body region is a vessel comprising an occlusion.

In another aspect, the first longitudinal member is configured to approach the body region in an antegrade fashion and the second longitudinal member is configured to approach the body region in a retrograde fashion.

In another aspect, the energy source is a radiofrequency energy source and one of the conductive electrodes is an active electrode and another is a passive electrode. In one aspect, the composition is delivered in a direction from the active electrode to the passive electrode. In yet another aspect, the composition is delivered in a bi-directional fashion between the conductive electrodes. In still yet another aspect, the composition is a conductive fluid and the conductive fluid forms an energy path between the conductive electrodes, wherein the energy path is configured to facilitate energy transmission between the conductive electrodes. In another aspect, the conductive fluid energized by the energy field is configured to ablate a portion of the body region.

In one aspect, the device comprises at least one composition reservoir configured to hold the composition, wherein the composition reservoir is connected to the delivery element through one or more lumens disposed within at least one of the longitudinal members.

In another aspect, the longitudinal members may be configured as guidewires, catheters, micro-catheters, or dilating catheters.

In another aspect, the energy source is configured to generate an electric field, a magnetic field, or ultrasonic field.

In one aspect, the composition is isotonic saline, in another aspect, the composition is collagenase, in yet another aspect, the composition is a biocompatible gas.

Present embodiments also disclose a device for recanalizing an occluded vessel. In one aspect, the device comprises a first longitudinal member capable of being advanced in an antegrade fashion through a proximal end of the occlusion, a second longitudinal member capable of being advanced in an retrograde fashion through a distal end of the occlusion, wherein at least one of the longitudinal members further comprises a delivery element configured to deliver at least one composition to the occluded vessel, such that the one or more composition is delivered to treat the occluded vessel.

Other aspects of the invention include methods corresponding to the devices and systems described above.

BRIEF DESCRIPTION OF THE DRAWINGS

The invention has other advantages and features which will be more readily apparent from the following detailed description of the invention and the appended claims, when taken in conjunction with the accompanying drawings, in which:

FIGS. 3A-3B show various embodiments of longitudinal members comprising insulators.

DETAILED DESCRIPTION

Figure 1:
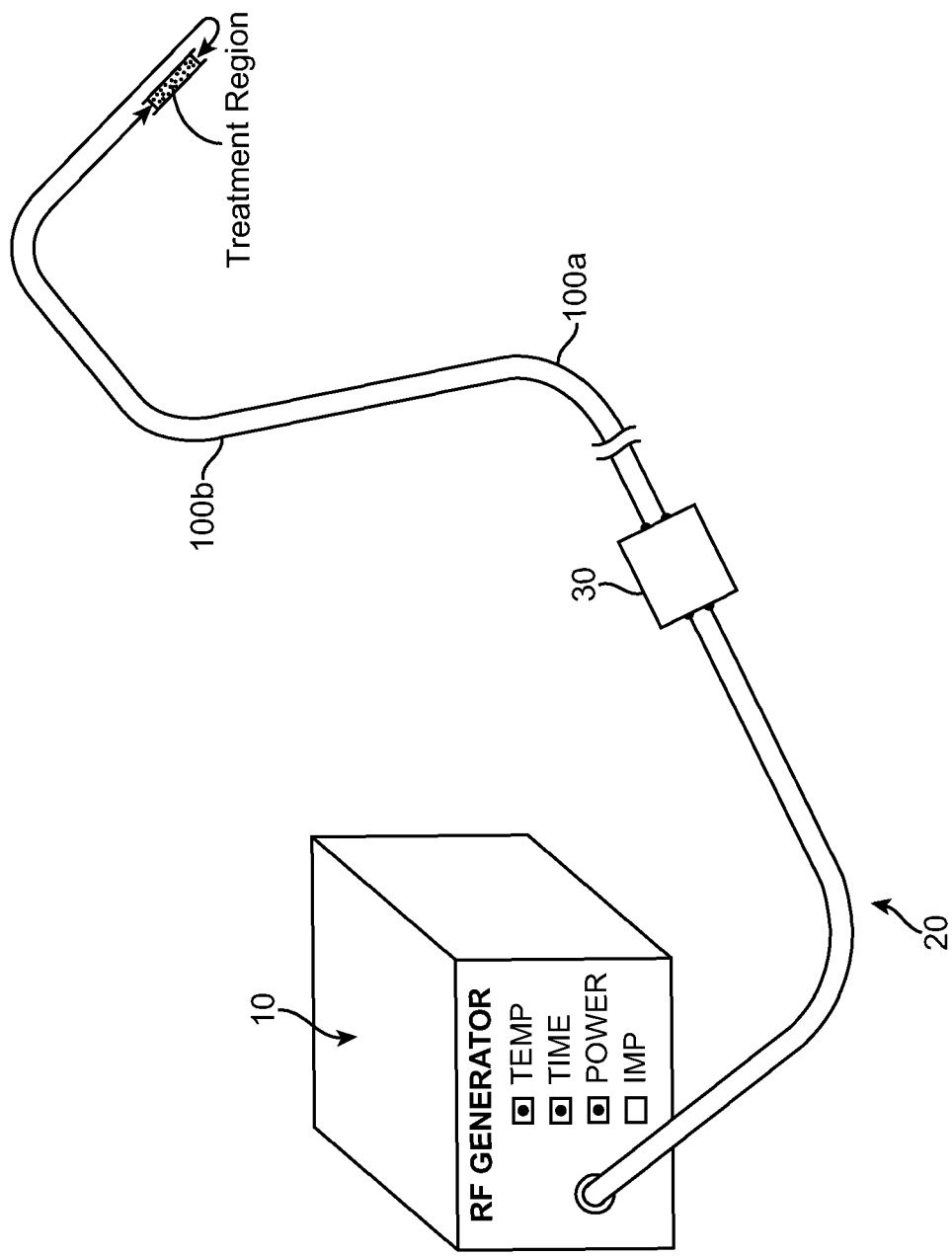
FIG. 1 is a schematic showing an RF generator connected to the longitudinal members.

Although the detailed description contains many specifics, these should not be construed as limiting the scope of the disclosure but merely as illustrating different examples and aspects of the disclosure. It should be appreciated that the scope of the disclosure includes other embodiments not discussed herein. Various other modifications, changes and variations which will be apparent to those skilled in the art may be made in the arrangement, operation and details of the method and apparatus disclosed herein without departing from the spirit and scope of the disclosure as described here.

The present embodiments relate to systems, devices, and methods of delivering one or more compositions to a hollow body treatment region. Specifically, one embodiment of the present disclosure relates to using multiple energy delivery longitudinal members to create an energy field whereby a composition is delivered to the treatment region at a rate or in a direction influenced by the generated energy field.

As referred to herein, a hollow body region includes any vessel or artery in which blood flows through a hollow tubular cavity as well as any duct or lumen within the body. In one embodiment, the hollow body region is a body vessel comprising an occlusion. An occluded body vessel may obstruct the blood flow and could have fatal consequences. Typically, the occlusion comprises a distal cap, a proximal cap, and an occlusion body therebetween. The occlusion could be atheromatous plaque, old thrombus, or similar other deposits.

As disclosed in U.S. Pat. No. 7,918,859 by the same inventors, which is incorporated herein in its entirety, in the controlled antegrade and retrograde tracking (CART) technique the retrograde approach takes advantage of an inter-coronary channel. Such a channel may be an epicardial channel, an inter-atrial channel, an intra-septal channel (also referred to as septal collateral), or a bypass graft. The basic concept of the CART technique is to create a channel through an occlusion, preferably with limited dissections, by approaching the occlusion both antegradely and retrogradely.

While the combined antegrade and retrograde approach has been effective in crossing difficult to cross lesions, it has been observed that using energy, for example radiofrequency (RF) energy, to ablate or alter the tissue in a controlled fashion is beneficial in crossing hard to cross lesions. Such controlled energy deployment is achieved using a bipolar arrangement of the electrodes, where one electrode is located on the antegrade element and the other electrode that constitutes the bipolar arrangement is located on the retrograde element. These electrodes can also be referred to as the return and active electrodes. They are also referred to as the anode and cathode, respectively. The electrodes could also be arranged in an array (multiple electrodes), where the electrode arrangement provides better control over the depth of penetration of the RF field and thereby provides the ability to control the tissue temperature.

By taking advantage of an antegrade and retrograde approach to establish a bipolar electrode arrangement across the occlusion, it is possible to leverage the generated energy field to recanalize difficult to cross occlusions. This approach minimizes the potential of the vessel wall becoming perforated or injured, as may otherwise occur in a conventional bipolar energy treatment approach, where both electrodes are on the same side of the occlusion. Because the electrodes are distributed on opposite sides of the occlusion, the tissue that is ablated by the energy treatment (i.e., the occlusion) is well contained between the electrodes. This also allows the user to localize the treatment to the occlusion.

To facilitate the bipolar energy delivery treatment, present embodiments contemplate delivering one or more compositions to a treatment region such as an occluded vessel. An energy field generated by the bipolar electrode arrangement of the longitudinal members is configured to affect, propel, or influence the rate and/or the direction that the compositions migrate within or through the treatment region. The composition may be conductive fluid, which may facilitate energy delivery between the longitudinal members and ablation by creating an energy sink and/or a conductive fluid path between the longitudinal members. Additionally or alternatively, the composition may be configured as a therapeutic agent, such that the therapeutic agent may be delivered to the treatment region under the influence of and facilitated by the generated energy field. Additionally, the composition may also be configured as a contrast agent or visualization agent.

FIG. 1 shows a system for delivering a composition to a treatment region, such as an occluded vessel facilitated by an energy modality. The system comprises longitudinal members 100a and 100b for delivering energy, such as RF energy, to the treatment region. As indicated in FIG. 1, the first longitudinal member 100a serves as an antegrade member, such that the first longitudinal member 100a is configured to approach the treatment region in an antegrade fashion, and the second longitudinal member 100b serves as a retrograde member, such that the second longitudinal member 100b is configured to approach the treatment region in an retrograde fashion.

An energy source, such as a source that provides an electric field, a magnetic field, high energy waves like laser or ultrasonic energy, of a combination thereof is configured to be connected to the longitudinal members 100a and 100b. In one embodiment, the energy source is an RF generator 10 (also referred to as a controller) which serves as the source of RF energy. Optionally, the RF generator may be a hand-held battery-operated device. Longitudinal members 100a and 100b may be guidewires, catheters, micro-catheters, or dilating catheters. In a preferred embodiment, longitudinal members's 100a and 100b are guidewires. Additionally, longitudinal members 100a and 100b are configured to have sufficient torsional rigidity and longitudinal flexibility to advance through tortuous anatomy or dense materials such as an occlusion, and to align their electrodes in a direction away from tissues such as the vessel wall, towards the other longitudinal member, or any combination thereof.

Figure 2:
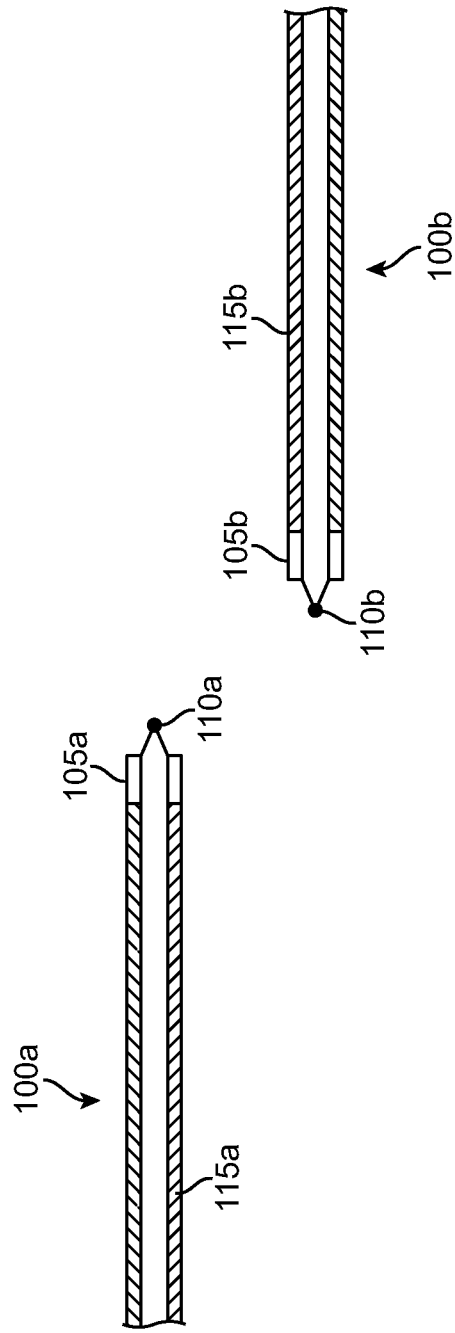
FIG. 2 shows one embodiment of the longitudinal members.

As shown in FIG. 2, the longitudinal members 100a and 100b have conductive electrodes 105a and 105b, respectively, at their distal ends. In one embodiment, where the treatment region is a occluded vessel, the electrodes 105a and 105b are located on one side of their respective longitudinal members 100a and 100b, thereby providing the operating physician with the freedom to allow the electrode-free side of the longitudinal members to touch the vessel wall (if needed) while still directing the RF energy away from the vessel wall. Additionally, this allows the configuration to direct the RF energy away from the vessel wall, thereby minimizing potential RF injury to the vessel wall. In one embodiment, one or more of the longitudinal members comprises a plurality of electrodes arranged in an array.

Conductive wires (not shown) connect the electrodes 105a and 105b of the longitudinal members, respectively, to connector 30 to deliver RF energy from the RF generator 10 to the electrodes 105a and 105b. The exterior of the longitudinal members are covered by non-conductive layers 115a and 115b, respectively, which sandwich the conductive wires between the longitudinal members and the non-conductive layers. In one embodiment, the non-conductive layers 115a and 115b comprise a sheath or a coating. Examples of materials may include Teflon, ceramic, polyimide, parylene, or other suitable materials. Examples of methods which could be employed for coating may include spraying, dipping, vapor deposition, or plasma deposition. In another embodiment, the conductive wires are insulated by using a heat resistant material on the guidewire to protect the device and surrounding tissue from excessive heat.

FIG. 3A shows a cross-sectional view of a longitudinal member comprising an electrode and an insulator, in accordance with an embodiment of the present invention. A longitudinal member 200 comprises an electrode 210 as its distal tip. The electrode 210 is electrically coupled to the longitudinal member's corewire via an electrically conductive ribbon 220 or other such electrically conductive connector. An insulator 230 is disposed at a distal portion of the guidewire 200 to deflect some of the heat that is generated when the electrode 210 is energized with radiofrequency energy, thereby protecting the rest of the device from such heat. The insulator 230 may wrap around the distal portion of the longitudinal member 200, as shown in FIG. 3A, or it may be configured as a plurality of discrete pieces disposed at the distal portion of the guidewire 200. The insulator may or may not directly contact electrodes.

In another embodiment, the insulator may be configured to protrude forward so that the electrode is recessed. An example of this is shown in FIG. 3B, showing a protruding insulator 240 configured to extend beyond the electrode 210, thereby recessing the electrode 210. This limits the exposure of the electrode 210 to surrounding tissue, while leaving the electrode sufficiently exposed to create the bipolar arrangement.

To provide RF energy from the RF generator 10 as seen in FIG. 1, to the longitudinal members 100a and 100b, a pigtail 20 connects at its proximal end to the RF generator 10 and terminates at its distal end in a connector 30. Connector 30 is a standard connector that couples the input and output signals of the RF generator 10 to the longitudinal members 100a and 100b.

One embodiment of the connector would be a locking tool or torque device which can be placed over the guidewire. In such a configuration, the locking tool or torque device is configured to make electrical contact with a portion of the longitudinal member (such as corewire) that conducts radiofrequency energy to, or from, the one or more electrodes disposed on the longitudinal member. In such a configuration, the locking tool or torque device would also be configured to connect to a radiofrequency generator, thereby electrically connecting the generator to the longitudinal member and electrodes. Means of locking the connector to the guidewire may include compressible prongs, screws, sliding rings, or other mechanisms commonly utilized in torque devices.

In one embodiment, and as further shown in FIG. 2, the longitudinal members 100a and 100b comprise temperature measuring elements 110a and 110b at the distal tip of the antegrade and retrograde longitudinal members, respectively. In one embodiment, the temperature measuring elements 110a and 110b comprise thermocouples or thermistors that are connected to the connector 30. In another embodiment, pressure measuring elements are placed on the distal ends of the guidewires to detect a change in pressure upon activation of the RF energy.

RF generator 10 is configured to allow the user to set a maximum temperature, a treatment time period, a level of RF power, or a combination of these control parameters. The treatment time period indicates the period of time over which the RF energy will flow between the electrodes. The maximum temperature setting serves as a threshold temperature for the tissue that is in contact with the electrodes, and the RF generator 10 can be set to reduce or shut off power to one or both electrodes when one or more of the temperature measuring elements 110a and 110b indicate a tissue temperature at or near the threshold.

In one embodiment, the generator 10 is capable of measuring the impedance of the tissue between the two electrodes 105a and 105b. Based on the type of the occlusion (i.e., the nature of the calcified material), the user can choose the appropriate combination of temperature, treatment time, and the amount of RF energy to be provided to the tissue to achieve a safe and effective treatment. Alternatively, the treatment may proceed with the user manually controlling the parameters during the recanalization procedure, with the user treating the occlusion until recanalization is achieved.

Figure 4:
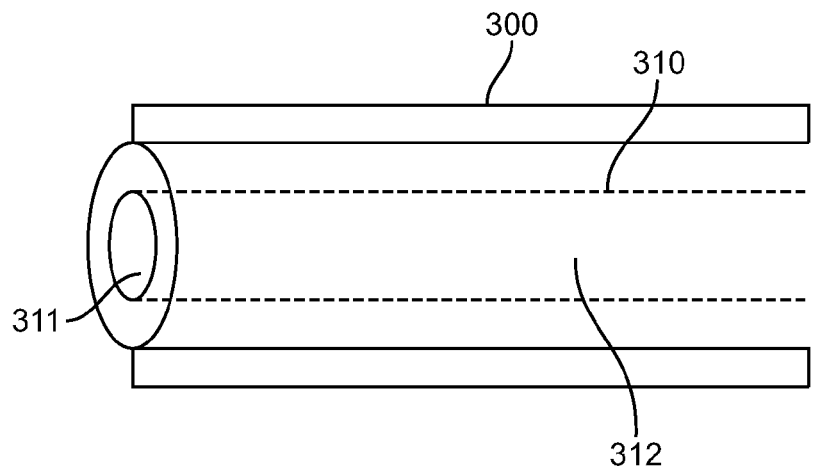
FIG. 4 show one embodiment of the longitudinal member comprising a composition delivery element.

One or both of the longitudinal members further comprise at least one delivery element configured to deliver one or more compositions to the treatment region. As seen in FIG. 4, in one embodiment, the delivery element is disposed within the interior of the longitudinal member. In one embodiment, the delivery element 310 comprises a distal delivery port 311 disposed substantially near the distal end of the longitudinal member 300, a proximal supply port (not shown), and a delivery shaft 312 disposed in-between. The supply port is configured to be connected with one or more composition reservoirs and/or other delivery mechanisms. The delivery port 311 is configured to deliver at least one composition to the treatment region, wherein the composition may be transmitted to the delivery port 311 from the composition reservoirs through the delivery shaft 312.

Additionally or alternatively, the delivery element 310 may comprise an injection port (not shown) that traverses the coating of the longitudinal member 300 to connect one or more composition reservoirs with the delivery shaft 311 of the delivery element 300. In such embodiment, the delivery shaft 311 may be coated with materials, such as hydrophobic materials that are configured to prevent the composition from exiting the delivery shaft 311.

Figure 5A:
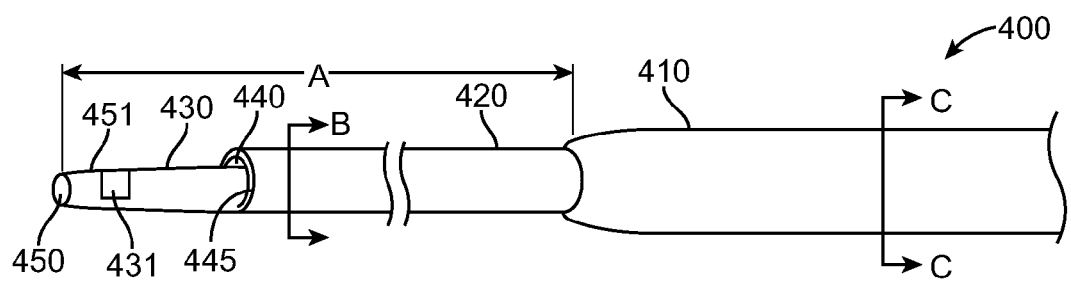
FIGS. 5A-5C show various views of one embodiment of a delivery catheter.

Alternatively, the delivery element may be independent of the longitudinal member. In one example, present embodiments contemplate a multi-lumen delivery catheter configured to accommodate a longitudinal member and/or a delivery element, as well as acting as the delivery element. As seen in FIG. 5A, the multi-lumen catheter comprising catheter shafts 410, 420, and 430. The inner shaft 430 as defined by a guidewire lumen 450 and a thin wall 451 is configured as a guidewire shaft to accommodate the longitudinal member. The delivery element comprises a delivery port 440 and a delivery shaft that is defined by the wall 451 of the inner shaft 430 and wall 445 of shaft 420. Inner shaft 430 extends the entire length of catheter 400. To facilitate identification of the location of the delivery catheter 400, inner shaft 430 may contain a radiopaque marker 431 adjacent to the distal tip of inner shaft 430.

Figure 5B:
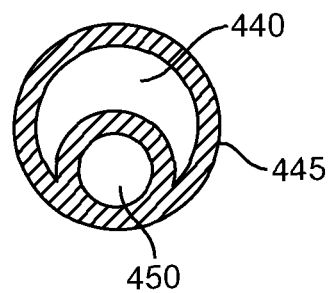
Figure 5C:
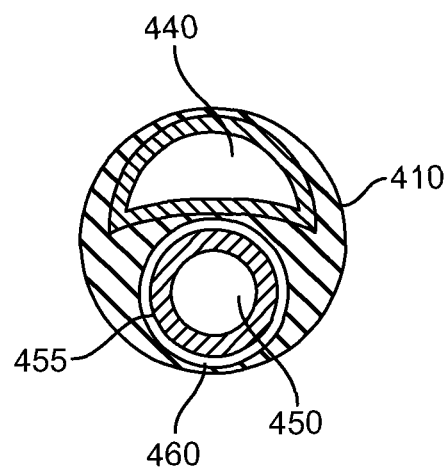

FIG. 5B shows the cross-section of shaft 420. FIG. 5C shows the cross section at the proximal end of the catheter 410. Each of shafts 410, 420, and 430 can be made of any number of polymers including but not limited to nylon, PEBAX, polyurethane, polyethylene and polyimide. A composition that is injected at the proximal end of the catheter exits the delivery port 440. FIG. 5C also shows the guidewire lumen 450 and a guidewire channel with an optional braided lining 460 and an optional PTFE lining 455. A typical ID for the guidewire lumen 250 would be about 0.39 mm but can range from 0.15-1.0 mm. A typical OD for the catheter shaft 430 would be 0.83 mm but can range from 0.5-2.0 mm.

Often, the passageways to the treatment region may be tortuous and impede the progress of the delivery catheter. Therefore, the multi-lumen delivery catheter described above may be modified for improved maneuverability. In an alternative embodiment of the delivery catheter, two shafts are detached from each other but are contained coaxially within one another. In such an embodiment, the inner shaft is the guidewire shaft, and the outer shaft is the delivery shaft. A composition is injected proximally into a supply port, travels through the space between the two coaxial shafts, and flows distally out of a delivery port. This coaxial arrangement allows the two lumens to retain their functionality, while decreasing the rigidity that would be created by an attached multi-lumen configuration. Furthermore, having the composition and the longitudinal member in separate lumens further enhances guidewire maneuverability. The added maneuverability and flexibility decreases the likelihood of the catheter kinking as it navigates tortuous pathways, thereby allowing for improved access to the treatment region as well as improved delivery of the composition.

Figure 6A:
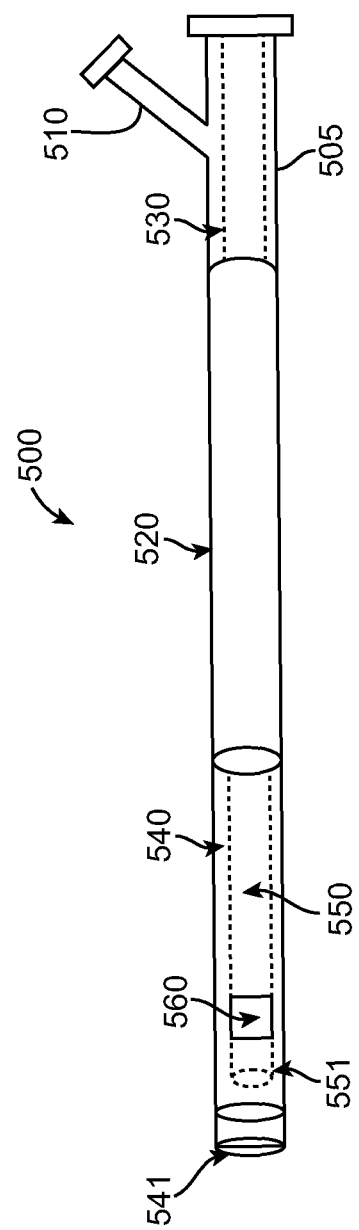
FIGS. 6A-6B show various views of another embodiment of a delivery catheter with coaxial shafts.

FIG. 6A shows an exemplary embodiment of such a delivery catheter having a coaxial multi-lumen configuration. The delivery catheter comprises a delivery shaft 520, and an inner guidewire shaft 530. The inner diameter of delivery shaft 520 is larger than the outer diameter of guidewire shaft 530, such that guidewire shaft 530 resides coaxially within delivery shaft 520, but is not attached to injection shaft 520. The proximal end of guidewire shaft 530 is coupled to a hub 505, whereas the distal end of the guidewire shaft 530 is free-floating within delivery shaft 520. Delivery shaft 520 comprises a wall 541 and a delivery shaft lumen 540. Guidewire shaft 530 comprises a wall 551 and a guidewire lumen 550. A composition, when injected proximally into supply port 510, travels through the space between the two shaft walls 551 and 541, and flows distally out of the delivery catheter 500. Optionally, the distal tip of the guidewire shaft 530 or the delivery shaft 520 may comprise a radiopaque marker 560, as shown.

In the embodiment shown in FIG. 6A, the length of guidewire shaft 530 is shorter than the length of delivery shaft 520. Alternatively, the length of guidewire shaft 530 may be longer than the length of delivery shaft 520, or the same length as the delivery shaft 520.

Figure 6B:
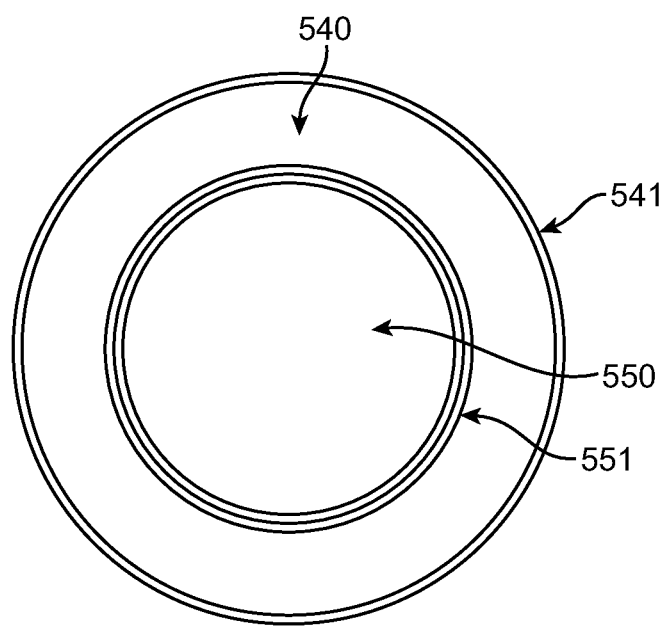

FIG. 6B shows a cross-section of the delivery device of FIG. 6A, showing delivery and guidewire shaft walls 541 and 551, and delivery and guidewire lumens 540 and 550. Each of the shaft walls 541 and 551 may be made of one or more polymers, including but not limited to nylon, PEBAX, polyurethane, polyethylene and polyimide. Optionally, the inside of the guidewire shaft wall 551 is lined with a material having a low coefficient of friction, for example PTFE or high-density poly-ethylene, to facilitate movement of the longitudinal member within the guidewire lumen 550.

Optionally, the guidewire shaft 530 and/or the delivery shaft 520 may comprise a plurality of segments made of materials with differing durometers, thereby allowing finer control of the flexibility along the length of the shaft. For example, in one embodiment, the proximal end of the guidewire shaft 530 may comprise a braid, increasing the rigidity and allowing a user to advance the delivery catheter by providing a force proximally, whereas the distal end of the guidewire shaft 530 may comprise a coil, increasing the flexibility and allowing the delivery catheter to follow tortuous passageways without kinking Optionally, the leading edge of the delivery catheter may comprise a soft tip to promote maneuverability and prevent damage to the vessel wall.

The composition reservoir may be configured as an intravenous drip bag, a pressurized intravenous drip bag, a locking syringe, drug cartridge, or the like. Optionally, supply port or injection port as described above may be pressurized to facilitate a continuous flow of the composition from the reservoir.

Optionally, the proximal opening of the delivery element may be configured to connect to the composition reservoir via a delivery controller, wherein the delivery controller is configured to control composition delivery. In one embodiment, the delivery controller may be configured to control the rate of the composition delivery and the amount of composition delivered to the treatment region. Additionally, the delivery controller may be connected to two or more composition reservoirs which hold different compositions. In such embodiment, the delivery controller enables the operator to choose which composition to deliver to the treatment region.

In one embodiment, the delivery controller comprises a drive mechanism for discharging the composition from the composition reservoir. In one embodiment, the drive mechanism comprises a precision screw that is configured to transmit movement to a vertical micro-lever, which activates a plunger, stem and piston against the composition reservoir. The drive mechanism further comprises a micromotor configured to drive the composition to the delivery element. In one embodiment, the rotation of the micromotor is designed to be unidirectional, which prevents backward movement or the stem, thereby preventing negative pressure build-up and undesirable reverse inflow of fluids back into the composition reservoir. Additionally and optionally, the delivery controller may further comprise one or more microcontrollers comprising CPU, clock, memory and/or user interface. The microcontroller may be configured to control composition delivery from the reservoirs and may be programmed to store one or more dosing parameters or treatment schedules.

The conductive electrodes disposed on the longitudinal members are configured to generate an energy field, such as an RF energy field, whereby under the influence of the energy field, the composition delivered by the delivery element is configured to substantially migrate either in the direction towards the active electrode or the passive electrode and/or facilitate the rate of migration. In one embodiment, it is contemplated that a composition delivered through one or more delivery elements may facilitate energy delivery across the electrodes.

In one embodiment, the composition is configured as a conductive fluid. A conductive fluid may be any fluid comprising positive or negative charges, such as isotonic saline. In one embodiment, the conductive fluid may be delivered to the treatment region through the longitudinal member comprising the passive electrode, the conductive fluid thereby immerses a portion of the treatment region such that the active electrode disposed on the other longitudinal member may generate a current density that is sufficiently high to cause sparks crossing over to the fluid immersed portion of the treatment region. In such an embodiment, the fluid may acts as an energy sink, thus receiving the energy delivered from the active electrode.

In another embodiment, the conductive fluid may migrate through the treatment region influenced or facilitated by the energy field created by the electrodes. For example, a negatively charged conductive fluid may be delivered to the treatment region from one longitudinal member whereby the negatively charged conductive fluid is attracted and migrates towards the positive charge generated by the other longitudinal member. Alternatively, a positively charged conductive fluid may be delivered to the treatment region whereby the fluid is attracted and migrates towards the negative charge generated by the longitudinal member. Furthermore, the composition may be delivered in a bi-directional fashion between the first and longitudinal members. The migration of the conductive fluid forms a conductive fluid path between the longitudinal members which may facilitate energy delivery between the longitudinal members. In one embodiment, the conductive fluid may penetrate at least a portion of the occlusion in the vessel by traversing substantially through pores or channels in the occlusion, thereby creating a conductive fluid path within or through the occlusion.

Furthermore, it is envisioned that the energy as applied from the electrodes may be sufficient to energize the conductive fluid such that the conductive fluid may ablate materials in contact with the fluid. For example, the energy as applied from the electrodes may be sufficient to heat the conductive fluid or vaporize the conductive fluid such that plasma may be formed to cause disintegration or breakdown of the occlusion in contact with the plasma. In one embodiment, a conductive fluid path may be initially created by applying energy through the electrodes to create an energy field that drives or propels the migration of the fluid. Thereafter, the energy as applied through the electrodes may be increased such that at least a portion of the fluid along the conductive fluid path is at least partly vaporized to ablate the material along the fluid path.

Another embodiment of the present device, methods, and systems is configured to deliver a composition configured as a therapeutic agent to the treatment region by using an energy field to facilitate the composition delivery. In one embodiment, the therapeutic agent may be configured as a charged compound, such that after the therapeutic agent has been delivered through the delivery element, the therapeutic agent is configured to migrate under the influence of the energy field as generated by the electrodes. Additionally or alternatively, a electrically neutral therapeutic agent may be modified by adding a charged moiety such that the modified therapeutic agent comprising the charged moiety may be more susceptible to the influence of the energy field. Additionally, the therapeutic agent may be submerged of dissolved in a conductive fluid, whereby the conductive fluid path under the influence of the energy field as described above serves as a vehicle to facilitate the delivery of the therapeutic agent to the treatment region.

It is contemplated that the therapeutic agent may be any composition that has a therapeutic effect to the treatment region. For example, therapeutic agent may be collagenase, or various other drugs or therapeutic substances.

In another embodiment the composition delivered to the treatment region may be used as a coolant to control the temperature of the treatment region during the ablation procedure. Additionally and optionally, the composition delivered to the treatment region may be used to weaken and/or break up a portion of the tissue to facilitate further treatments. For example, to treat an occluded vessel, the composition may be configured as compressed biocompatible gas such as $CO_2$, and the compressed gas is delivered into the occlusion before or during the advancement of the longitudinal member to create, enlarge, or expand a space in the occlusion to facilitate further penetration of the occlusion by the longitudinal member or composition delivery. Furthermore, it is contemplated that the composition may be a contrast agent configured to aid in visualization of the treatment region. For example, delivering a contrast agent at the appropriate location may reveal the available septals to facilitate identification of an appropriate channel while simultaneously advancing and manipulating the longitudinal members.

It is further contemplated that multiple compositions may be delivered in sequence or in tandem to the treatment region. In one embodiment, where the treatment region is an occluded vessel, a first composition configured to weaken and/or break up a portion of the occlusion is first delivered to the treatment region. As described above, the first composition may create or expand a space in the occlusion. Thereafter, a second composition is delivered to the treatment region. The second composition may migrate into the occlusion through the space affected by the first composition, thus facilitating the delivery of the second composition into the occlusion. In one embodiment, the second composition is configured as a conductive fluid, and the conductive fluid may deposit at least partly within the space affected by the first composition and thereafter acts as an energy sink by receiving the energy delivered from the active electrode. The conductive fluid may also form a conductive fluid path traversing at least partly through the space affected by the first composition. In another embodiment, the second composition may be a therapeutic agent as described above. The space affected by the first composition may act as a depository for the therapeutic agent into the treatment region or it may facilitate the therapeutic agent delivery through the occlusion as driven by the energy field as applied by the electrodes.

In another embodiment, the first composition may be a conductive fluid configured to facilitate energy ablation as described above. After the ablation process has been at least partly carried out, a second composition configured as a therapeutic agent may be delivered to the treatment region where the therapeutic agent may be deposited or delivered through the space created by the ablation process. Additionally or alternatively, the therapeutic agent may be applied initially, and the conductive fluid may be delivered thereafter. It is contemplated that multiple therapeutic agents may be delivered to the treatment region. Furthermore, more than two compositions may be used, for example, the first composition may be delivered to create or expand a space in the occlusion, a second composition may be delivered to facilitate energy conduction, and a third composition may be deliver as a therapeutic agent to further treat the occlusion.

It is contemplated that multi composition delivery may be achieved by using the delivery controller and multiple composition reservoirs. For example, the sequence of delivering multiple compositions may be programmed and stored within the memory of the microcontroller of the delivery controller, such that the microcontroller may automatically select the type and amount of the composition delivered depending on the programmed treatment regime.

Figure 7:
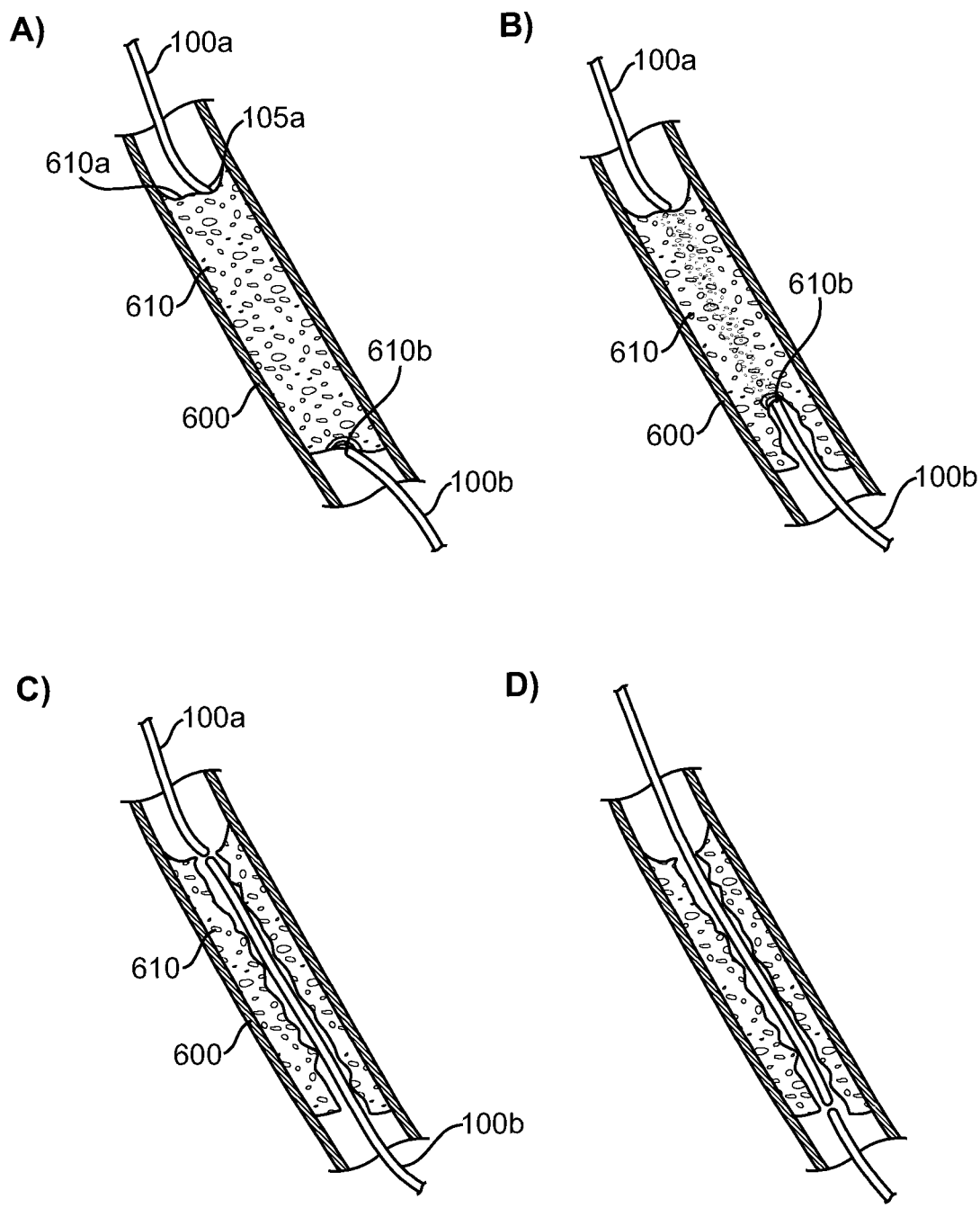
FIGS. 7-8 show steps of delivering a composition to an occluded vessel to aid in vascular recanalization.
Figure 8:
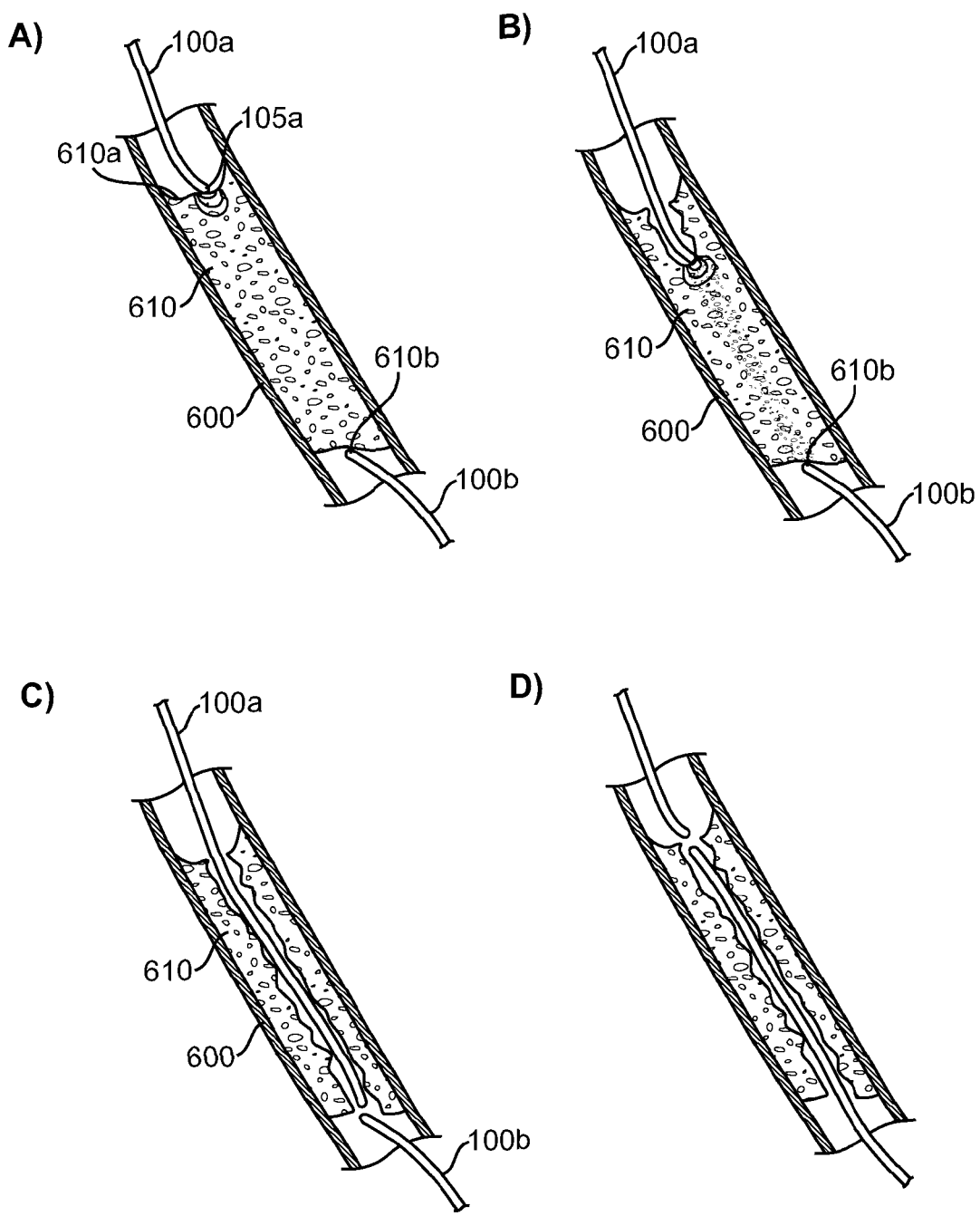

One exemplary sequence of treating an occluded vessel using one embodiment of the composition delivery device is illustrated in FIGS. 7 and 8. As shown in diagram A of FIG. 7, the first longitudinal member 100a and second longitudinal member 100b are advanced to the proximal and distal ends 610a and 610b of the occlusion 610, respectively. This can be accomplished using standard angioplasty techniques. As described in the above referenced U.S. Pat. No. 7,918, 859, the first longitudinal member may be a retrograde longitudinal member, which can be advanced to the distal end of the occlusion 610b using collaterals such as the septals. Additionally and optionally, a composition configured to weaken and/or break up a portion of the occlusion may be delivered to the occlusion through the delivery element prior to and/or contemporaneous with the advancement of the longitudinal members.

Once the operator has confirmed that the longitudinal members 100a and 100b are in contact with the occlusion 610 and are not touching the vessel wall 600, a RF energy field is generated through the electrodes disposed on the longitudinal members. Prior to and/or contemporaneous with generation of the RF energy field, a composition configured as a conductive fluid may be delivered to the treatment region such that the conductive fluid may act as an energy sink, which may help sustain or amplify the generated RF energy field.

Alternatively, the longitudinal members are advanced as deep into the occlusion as possible to minimize the distance between the electrodes and, consequently, minimize the length of the energy field. Again, a composition configured to weaken and/or break up a portion of the occlusion may be delivered to the occlusion through the delivery element prior to and/or contemporaneous with the advancement of the longitudinal members. Confirmation that the longitudinal members 100*a* and 100*b* are in an appropriate position can be generated by impedance measurements and/or by using any of the standard imaging techniques employed during interventional procedures, such as fluoroscopy or intravascular ultrasound (IVUS), in which transducers are placed on the distal ends of the longitudinal member. When using tissue impedance measurements, the calcified occlusion 610 generally exhibits significantly higher impedance than the vessel wall 600. If an impedance measurement indicates a low impedance value, it is likely that one or both longitudinal members are in contact with the vessel wall 600, and appropriate repositioning of the longitudinal members may be warranted.

It is further noted, that it may not be required for the longitudinal members to penetrate the occlusion to create an energy field. In fact, it may be sufficient for the longitudinal members to be positioned within proximity where the RF spark may cross from the active electrode disposed on one longitudinal member to the return electrode disposed on the other longitudinal member to achieve the energy field. For example, the second longitudinal member may be positioned within the distal true lumen of the occluded vessel, and the first longitudinal member may be positioned within the occlusion, RF energy may then be delivered between the active and return electrodes to create an energy field between the two longitudinal members.

Upon initiating the RF energy field, a composition configured as a conductive fluid may be delivered into the occlusion such that the conductive fluid forms a fluid path under the influence of the energy field. For example, the conductive fluid may migrate from a position at or close to the passive electrode towards the active electrode, while traversing at least a part of the occlusion. The conductive fluid path may facilitate energy transmission between the longitudinal members. Furthermore, the conductive fluid may absorb the RF energy along the conductive fluid path such that the fluid may be sufficiently heated or vaporized to form a plasma to cause disintegration or breakdown of the occlusion in contact with the fluid or plasma. In one embodiment, the occlusion 610 is ablated along the conductive fluid path from the ends 610*a* and 610*b* of the occlusion 610 to the interior of the occlusion 610, as shown in FIG. 7 diagram B.

Thereafter, the user then slowly and carefully advances one or both longitudinal members 100*a* and 100*b* until a channel or path is created in the occlusion 610, as shown in FIG. 7 diagram C. As shown in FIG. 7, the antegrade longitudinal member 100*a* may be kept stationary and the retrograde longitudinal member 100*b* may be advanced through the occlusion 610. Once a channel has been created, the retrograde longitudinal member 100*b* may be withdrawn and the antegrade longitudinal member 100*a* may be advanced through the occlusion 610, as shown in FIG. 7 diagram D, and standard interventional procedures, such as balloon angioplasty, can be performed. Alternatively, the retrograde longitudinal member 100*b* can be kept stationary during the RF treatment and composition delivery, where the antegrade longitudinal member 100*a* can be advanced through the occlusion 610. This is illustrated in FIG. 8 diagrams A-D.

Additionally or alternatively, during various steps of treatment, a composition configured as a therapeutic agent may be delivered into the occlusion such that the therapeutic agent migrates through the occlusion under the influence of the energy field.

It is noted that energizing an electrode with RF energy causes the electrode to generate heat. In general, the amount of such heat is proportional to the amount of radiofrequency energy delivered to the electrode, and inversely proportional to the surface area of the electrode. This is because the smaller the surface area of an electrode, the higher the current density passing through that surface area (for a given total current), which in turn causes the electrode to reach correspondingly higher temperatures. In one embodiment, the system is configured to deliver sufficient radiofrequency energy to an electrode such that radiofrequency sparks are generated.

While it is possible to have the surface areas of the active and return electrodes be of similar size, in a preferred embodiment an active electrode is configured to have a smaller surface area than a return electrode. This allows the active electrode to generate sufficient current or energy density to affect cutting or ablating and spark over to the return electrode, while at the same time allowing the return electrode surface area to be sufficiently large so as to maximize its contact with the occlusion and act as a sink for the energy emitted from the active electrode. Additionally, it is contemplated that a composition configured as a conductive fluid may be delivered through the longitudinal member comprising the passive electrode, such that the conductive fluid may act as an additional energy sink for the energy emitted from the active electrode. Another advantage of such an embodiment is that the return electrode will likely not reach as high temperatures as the active electrode. In addition, the conductive fluid may also acts as a heat sink or coolant for the passive electrode. In one embodiment, the ratio of the return electrode surface area to the active electrode surface area is configured to be in the range of about 50:1 to about 1:1, and preferably about 10:1. In one embodiment, the return electrode is configured in a pigtail design to increase surface area contact with the occlusion.

Figure 9A:
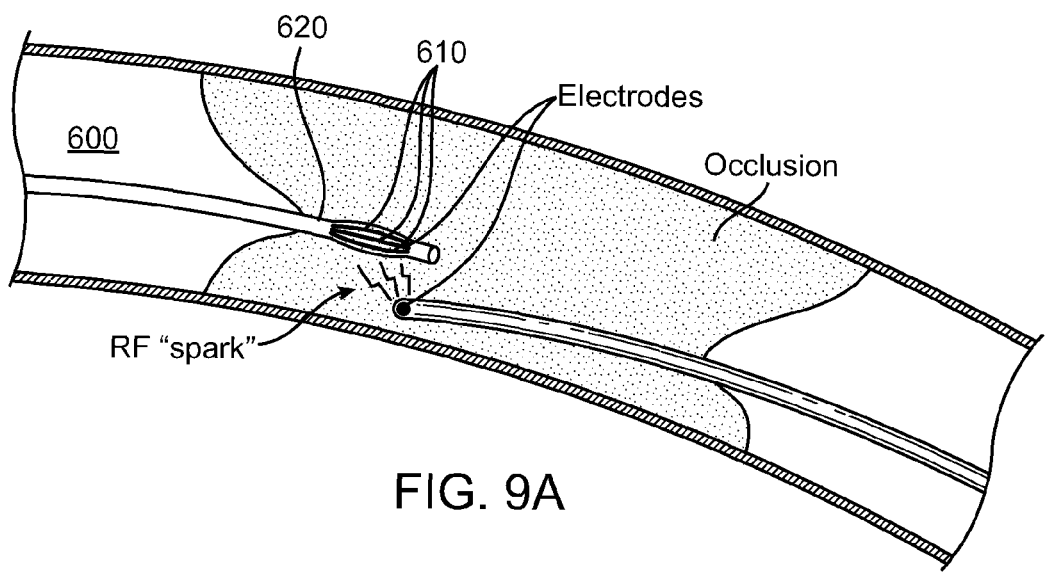
FIG. 9A-9C shows an exemplary embodiment of conductive electrodes configured to expand outwardly.
Figure 9B:
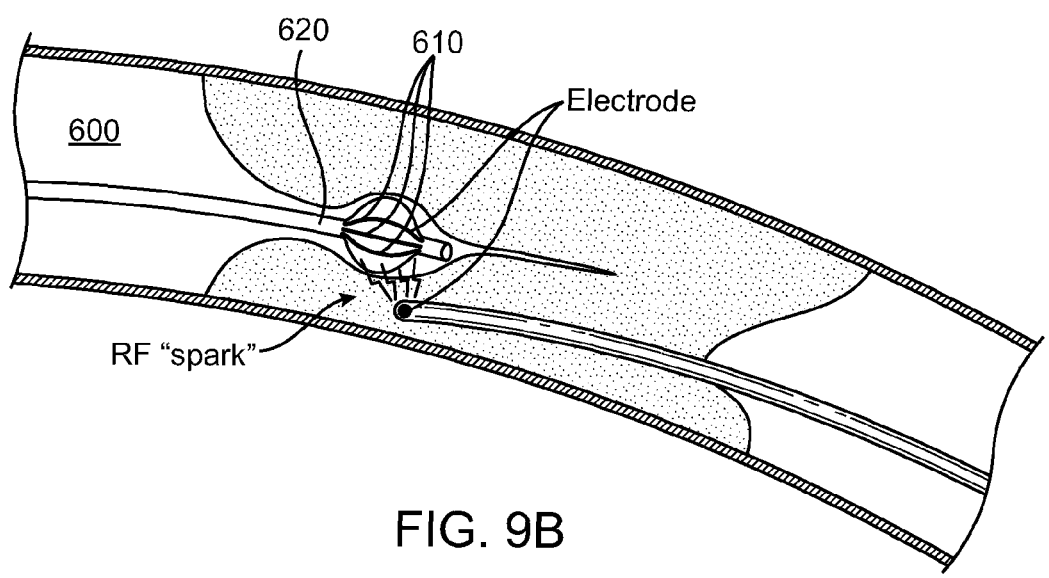

In another embodiment, a plurality of return electrodes may be configured to expand outwardly in order to spread out and increase surface area contact with the occlusion. Such an embodiment is shown in FIG. 9A, where a plurality of ribs 610 are disposed on a distal end 620 of a longitudinal member 600. The ribs 610 are configured to flare out, as shown in FIG. 9B. In a collapsed state, the ribs 610 are kept under tension, for example by using a restraining sleeve (not shown), by twisting the ribs 610, by exerting a stretching or pulling force on the proximal ends of the ribs 610, etc. The longitudinal member 600, with the ribs 610 in a collapsed state, is advanced into the occlusion. Upon releasing the tension or pulling back on the restraining sleeve, the ribs 610 flare open.

Figure 9C:
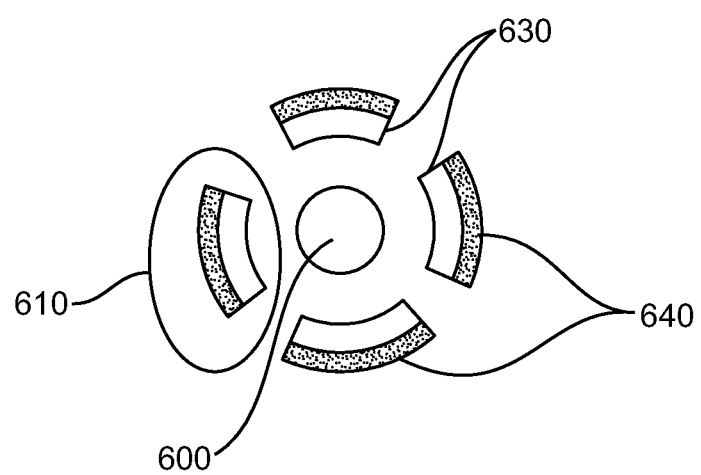

In another embodiment, the ribs 610 comprise electrode areas 630 adjacent to insulator areas 640, as shown in the cross-sectional view of FIG. 9C. In such an embodiment, when the ribs 610 flare out into a basket-like configuration, the insulator areas 640 are on the outside and the electrode areas 630 are on the inside of the basket-like configuration. This configuration advantageously aids in directing radiofrequency energy inside the basket-like configuration while simultaneously providing protection to the surrounding tissue. Alternatively, it is contemplated that in other embodiments the placement of the electrode areas 630 and insulator areas 640 may be varied. In an optional embodiment, a capture device may be configured to comprise one or more electrode areas for use as return electrodes. Examples of capture devices are disclosed in the co-pending U.S. patent application Ser. No. 12/150,111 by the same inventors, which is incorporated herein in its entirety.

Optionally, a centering balloon catheter can be utilized along with the longitudinal members to center the guidewire within the vessel prior to energizing the system. In such a configuration, it would be advantageous to have a heat resistant tip on the distal end of the balloon catheter.

Figure 10:
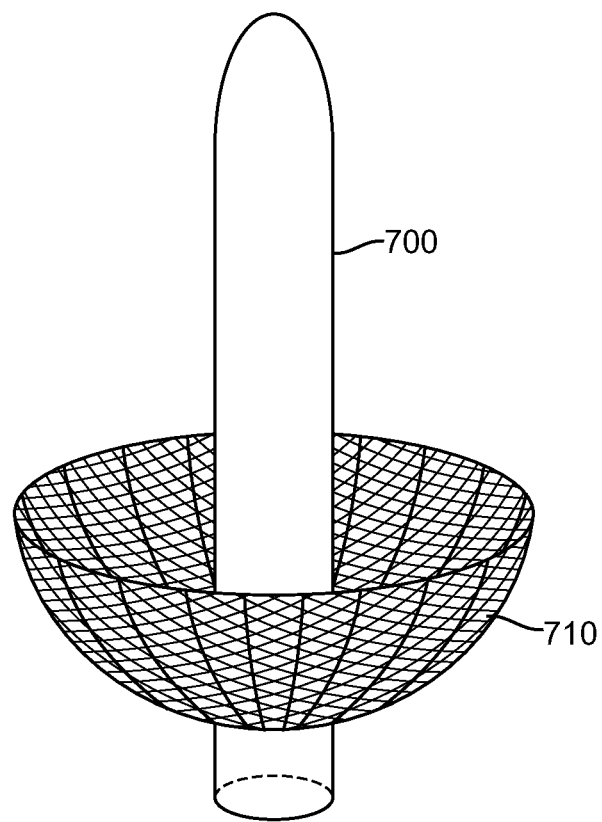
FIG. 10 shows an exemplary embodiment of a longitudinal member comprising an embolic protection mechanism.

Optionally, the catheter comprises a means for removing or withdrawing debris resulting from the RF ablation. For example, a mechanism could be provided to capture and retrieve the debris, or a suction device could be provided to actively remove the debris near the ablation area. Examples of such embolic protection mechanisms are disclosed in the above referenced U.S. Pat. No. 7,918,859. FIG. 10 shows an exemplary embodiment of a longitudinal member 700 comprising an embolic protection mechanism 710. The embolic protection mechanism 710 comprises a filter, mesh, net, or similar element, for capturing and retrieving ablation debris. As another example, the embolic protection may comprise a balloon for occluding the vessel and preventing the debris from circulating, and for subsequent aspiration of the debris through a longitudinal member. As another example, if a sheath is provided, such sheath may also be configured to be or to include a debris capture and retrieval mechanism or a suction device. In one embodiment, a longitudinal member may be retracted, and the remaining sheath may be used as a capture and retrieval mechanism or a suction device to remove ablation debris. In another embodiment, the longitudinal member comprises an ablating wire housed in the lumen of a dilating catheter. Upon ablation, the ablating wire may be retracted and the dilating catheter may be used to remove the debris. Alternatively, the system comprises a separate catheter to provide suction, or otherwise capture and remove the debris from the ablation site.

Optionally, present embodiments may be coupled to an electrocardiogram (EKG) machine to aid in timing energy emissions. For example, the rate of blood flow through the coronary arteries typically varies during the cardiac cycle. During systole when the heart is contracting, flow through the arteries is generally lower than during diastole. In one embodiment, energy emission is timed during diastole, for example using an algorithm to detect the R-wave of an EKG, and energy emission is timed to occur when flow is highest, thereby maximizing the cooling effect provided by blood flow and consequently minimizing the heat exposure to the vessel. Additionally, coronary artery dimensions can vary during the cardiac cycle and energy emission can similarly be timed to take advantage of this fact.

Optionally, present embodiments may be configured to perform an imaging function, such as intravascular ultrasound or optical coherence tomography (OCT). In one embodiment, this may be accomplished by adding a piezoelectric crystal to a longitudinal member of the device, wherein the piezoelectric crystal may be energized to transmit or receive ultrasonic waves. In another embodiment, an imaging core may be inserted into a longitudinal member of the device (e.g., in the case of a dilating catheter) and operated to transmit and receive ultrasonic waves. In another embodiment, an optical fiber may be used for performing OCT imaging.

Optionally, present embodiments comprise a mechanism for detecting or estimating the distance between the electrodes, and for decreasing the amount of delivered RF energy as the distance between the electrodes decreases, thereby minimizing potential RF injury to the vessel wall.

Various embodiments of the longitudinal members and electrodes may be made from any one or more suitable materials as is commonly known in the art. Examples of such suitable materials include stainless steel, Nitinol, Elgiloy, platinum, iridium, tantalum, titanium, cobalt, chromium, tungsten, or any combinations thereof. In one embodiment, one or more of the guidewires may be made of a polymer, with an electrically conductive core for transmitting electrical energy to the respective electrodes. The cross-sectional area of the longitudinal members and/or the delivery element may be configured to progressively increase from the distal end towards the proximal end. The tapered configuration may be advantageous in that the narrow distal end may be configured to effectively traverse through the tortuous tissue region such as vascular matrix and to penetrate the occlusion and/or the subintimal space, whereas the larger proximal end is configured to allow a user to manipulate the longitudinal members during the operation. Alternatively and optionally, a cross-sectional area of the longitudinal members may be configured to be substantially unchanged throughout the lengths of the longitudinal members.

It is noted that the flexibility of the longitudinal members may vary over their respective lengths. In one embodiment, the distal ends may be substantially flexible, and the flexibility progressively decreases towards the proximal ends.

Optionally, the longitudinal members of the present embodiments may comprise at least a layer of structural polymer over the core wire. Additionally and optionally, an outer surface of the longitudinal members may be coated with hydrophilic coating for ease of navigation through tortuous passageways.

In addition to the retrograde/antegrade approach as described above, it is contemplated that the present embodiments may be configured to deliver a composition to a treatment region such as an occluded vessel by penetrating the distal cap of the occlusion without approaching the distal cap from the retrograde direction through an intercoronary channel. Thereafter, one or more compositions may be delivered and RF energy may be delivered in a bipolar arrangement between two longitudinal members to generate an energy field as described above. As described in co-pending PCT application PCT/US2011/031018 by the same inventors, which is incorporated herein in its entirety, the distal end of one or more longitudinal members may be configured to be capable of being redirected. Similarly, present embodiments contemplate that at least a portion of the composition delivery element as disposed on the longitudinal member may likewise be redirected.

The present embodiments further contemplate delivering one or more compositions in conjunction to the antegrade and retrograde tracking (CART) techniques as disclosed in the U.S. Pat. No. 7,918,859. In such embodiments, a composition may be delivered during the various stages of the antegrade and retrograde procedures without using an energy modality. For example, a composition such as a biocompatible compressed gas may be delivered to the occluded vessel using the delivery element to create, enlarge, or expand a space in the occlusion to facilitate further penetration of the occlusion by the longitudinal member or composition delivery. Furthermore, a therapeutic agent such as collagenase may be delivered to the occluded vessel to soften the occlusion.

While the above embodiments refer to the use of RF energy for the purpose of generating an energy field and ablation, it should be noted that other energy modalities may be used as well. For example, in one embodiment, one or more longitudinal members comprise one or more ultrasound transducers, instead of or in addition to RF electrodes. The ultrasound transducers provide ultrasound energy for ablating an occlusion. In one embodiment, the antegrade and/or the retrograde longitudinal members may comprise ultrasound transducers and ablate the occlusion from an antegrade as well as a retrograde direction. Other energy modalities could include microwave and laser.

It should be noted that the combined antegrade and retrograde energy delivery techniques described above could also be used as an adjunct technique to crossing CTOs in combination with using conventional methods. The technique could be used to sufficiently soften or weaken the occlusion, thereby allowing a guidewire or catheter to cross the occlusion.

Additionally, it is noted that the present embodiments are applicable to various treatment regions, and are not limited to coronary occlusions. For example, present embodiments may be used deliver therapeutic or diagnostic agents to any site within the vascular system. For example, in oncology, one or both of longitudinal members may used to inject therapeutic agents such as 5FU, doxorubicin, adriamycin, etc. at the site of a tumor. As another example, in interventional neuroradiology, one or both of the longitudinal members may be used to diagnose or treat aneurysms or fistulas by delivering therapeutic or diagnostic agents including coils, polymers, gels, etc.

It is contemplated that the present embodiments may be used to deliver other therapeutic agents or other biologically active substances including but not limited to: amino acids, anabolics, analgesics and antagonists, anesthetics, anthelmintics, anti-adrenergic agents, anti-asthmatics, anti-atherosclerotics, antibacterials, anticholesterolics, anti-coagulants, antidepressants, antidotes, anti-emetics, anti-epileptic drugs, ant-fibrinolytics, anti-inflammatory agents, antihypertensives, antimetabolites, antimigraine agents, antimycotics, antinauseants, antineoplastics, anti-obesity agents, anti-Parkinson agents, antiprotozoals, antipsychotics, antirheumatics, antiseptics, antivertigo agents, antivirals, bacterial vaccines, bioflavonoids, calcium channel blockers, capillary stabilizing agents, coagulants, corticosteroids, detoxifying agents for cytostatic treatment, contrast agents (like contrast media, radioisotopes, and other diagnostic agents), electrolytes, enzymes, enzyme inhibitors, gangliosides and ganglioside derivatives, hemostatics, hormones, hormone antagonists, hypnotics, immunomodulators, immunostimulants, immunosuppressants, minerals, muscle relaxants, neuromodulators, neurotransmitters and nootropics, osmotic diuretics, parasympatholytics, para-sympathomimetics, peptides, proteins, respiratory stimulants, smooth muscle relaxants, sympatholytics, sympathomimetics, vasodilators, vasoprotectives, vectors for gentherapy, viral vaccines, viruses, vitamins, and the like.

While the above is a complete description of the preferred embodiments of the invention, various alternatives, modifications, and equivalents may be used. Therefore, the above description should not be taken as limiting the scope of the invention which is defined by the appended claims.

What is claimed is:

1. A method for delivering a composition to a body region, comprising:
   advancing a first longitudinal member coupled to an energy source and comprising a first conductive electrode into the body region;
   advancing a second longitudinal member coupled to the energy source and non-overlapping with the first longitudinal member into the body region, the second longitudinal member comprising a second conductive electrode, wherein the first longitudinal member or the second longitudinal member comprises a delivery element configured to deliver at least one composition to the body region;
   generating an energy field using the first conductive electrode and the second conductive electrode; and
   delivering the composition to the body region after generating the energy field such that migration of the composition in the body region is in a direction influenced by the generated energy field.

2. The method of claim 1, wherein the energy source is a radiofrequency energy source and the first conductive electrode is an active electrode and the second conductive electrode is a passive electrode.

3. The method of claim 1, wherein the delivering the composition further comprises delivering the composition in a direction from the first conductive electrode to the second conductive electrode.

4. The method of claim 1, wherein the delivering the composition further comprises delivering the composition in a bi-directional fashion between the first and second conductive electrodes.

5. The method of claim 1, further comprising transmitting the composition to the delivery element from at least one reservoir configured to hold the composition.

6. The method of claim 5, wherein the at least one reservoir is connected to the delivery element through one or more lumens disposed within the first or the second longitudinal members.

7. The method of claim 1, wherein the longitudinal members are guidewires, catheters, micro-catheters, or dilating catheters.

8. The method of claim 1, wherein the energy source is configured to generate an electric field, a magnetic field, or an ultrasonic field.

9. The method of claim 1, wherein the composition is a conductive fluid and the conductive fluid forms an energy path between the first conductive electrode and the second conductive electrode.

10. The method of claim 9, wherein the energy path facilitates energy transmission between the first and the second conductive electrodes.

11. The method of claim 9, wherein the conductive fluid is configured to ablate a portion of the body region.

12. The method of claim 9, wherein the conductive fluid is saline.

13. The method of claim 1, wherein the first longitudinal member is advanced into the body region in an antegrade direction fashion and the second longitudinal member is advanced into the body region in a retrograde direction fashion.

14. The method of claim 1, wherein the body region is a vessel comprising an occlusion.

15. The method of claim 1, wherein the composition is collagenase.

16. A method for delivering a composition to a body region, comprising:
   advancing a first longitudinal member coupled to an energy source and comprising a first conductive electrode into the body region in an antegrade direction;
   advancing a second longitudinal member coupled to the energy source and non-overlapping with the first longitudinal member into the body region in a retrograde direction, the second longitudinal member comprising a second conductive electrode, wherein the first longitudinal member or the second longitudinal member comprises a delivery element configured to deliver at least one composition to the body region;

generating an energy field using the first conductive electrode and the second conductive electrode; and delivering the composition to the body region in a direction based on the generated energy field.

17. A method for delivering a composition to a body region, comprising:

advancing a first longitudinal member coupled to an energy source and comprising a first conductive electrode into the body region, wherein the body region is a vessel comprising an occlusion;

advancing a second longitudinal member coupled to the energy source and non-overlapping with the first longitudinal member into the body region, the second longitudinal member comprising a second conductive electrode, wherein the first longitudinal member or the second longitudinal member comprises a delivery element configured to deliver at least one composition to the body region;

generating an energy field using the first conductive electrode and the second conductive electrode; and delivering the composition to the body region in a direction based on the generated energy field.

18. A method for delivering a composition to a body region, comprising:

advancing a first longitudinal member coupled to an energy source and comprising a first conductive electrode into the body region;

advancing a second longitudinal member coupled to the energy source and non-overlapping with the first longitudinal member into the body region, the second longitudinal member comprising a second conductive electrode, wherein the first longitudinal member or the second longitudinal member comprises a delivery element configured to deliver at least one composition to the body region;

generating an energy field using the first conductive electrode and the second conductive electrode; and delivering the composition to the body region in a direction based on the generated energy field, wherein the composition is collagenase.

* * * * *